United States Patent [19]

Marrone et al.

[11] Patent Number: 5,626,882
[45] Date of Patent: May 6, 1997

[54] METHOD OF USING EMU OIL AS AN INSECT REPELLENT

[75] Inventors: Pamela G. Marrone; Stephen A. Judd, both of Davis, Calif.

[73] Assignees: AgraQuest, Inc.; P.E. Zoogen, both of Davis, Calif.

[21] Appl. No.: 616,708

[22] Filed: Mar. 15, 1996

[51] Int. Cl.$^6$ .................................................. A61K 35/12
[52] U.S. Cl. ........................... 424/522; 424/DIG. 10
[58] Field of Search ............................ 424/522, 520, 424/DIG. 10

[56] References Cited

U.S. PATENT DOCUMENTS

| | | | |
|---|---|---|---|
| 5,208,209 | 5/1993 | Otsuji et al. | 503/221 |
| 5,346,922 | 9/1994 | Beldock et al. | 514/703 |

OTHER PUBLICATIONS

Wantanabe et al., "Rotundial, a new natural mosquito repellent from the leaves of *Vitex rotundifolia*" *Biotech Biochem.* (1995) 59(10):1979–1980.

Wantanabe et al., "New mosquito repellent from *Eucalyptus camaldulensis*" *J. Agric. Food Chem.* (1993) 41:2164–2166.

Sharma et al., "Mosquito repellent action of Neem" *Azadirachta indica* oil *J. Am. Mosquito Control Assn.* (1993) 9(3):359–360.

*Primary Examiner*—Raymond Henley, III
*Attorney, Agent, or Firm*—Morrison & Foerster

[57] ABSTRACT

This invention provides a method for repelling biting insects such as mosquitoes by topically applying emu oil to the skin.

1 Claim, No Drawings

METHOD OF USING EMU OIL AS AN INSECT REPELLENT

TECHNICAL FIELD

This invention is in the field of topical insect repellents. More particularly, an effective, natural and safe mosquito repellent comprising emu oil is provided.

BACKGROUND ART

This invention relates to a method of repelling insects, and more particularly to a method for repelling mosquitoes using a natural ingredient, emu oil. Known natural oils that repel insects include rotundial (from the leaves of *Vitex rotundifolia*, Watanabe K et al. (1995) *Biotech Biochem* 59(10):1979–1980); citronella oil (e.g. U.S. Pat. No. 5,346, 922); eucalyptus oil (Watanabe et al. (1993) *J. Agric. Food Chem.* 41:2164–2166); and oil (Sharma VP et al. (1993) *J. American Mosquito Control Association* 9(3):359–360); and oil of *Hedeoma pulgioides*, oil of anisum and oil of chrysanthemum (U.S. Pat. No. 5,208,209).

However, the only active ingredient currently registered by the EPA as a topically applied insect repellent is N,N-diethyl-m-toluamide (DEET). When applied to children's skin, DEET has been implicated in causing convulsions. DEET is also known to react with certain plastics and synthetic rubber and cause skin irritation (Watanabe et al. (1993), supra). As a result of these problems and other side effects, New York State has banned products comprised of 100% DEET.

Accordingly, there remains a need for a natural, safe substance which acts to repel biting insects when topically applied to the skin.

SUMMARY OF THE INVENTION

The present invention provides a method for repelling biting insects comprising the step of topically applying emu oil to the skin of a subject.

BEST MODE FOR CARRYING OUT THE INVENTION

Throughout this application, various publications, patents and published patent applications are referred to by an identifying citation. The disclosures of these publications, patents and published patent applications are hereby incorporated by reference into this application to more fully describe the state of the art to which this invention pertains.

The present invention provides a method of repelling biting insects using emu oil, a natural and safe substance. In the preferred embodiment, pure emu oil is applied to the skin.

The following examples are presented as a further guide to the practitioner of ordinary skill in the art, and are not to be construed as limiting the invention in any way.

Example 1

The effect of emu oil on frequency of mosquito lands and bites

To determine if emu oil was an effective mosquito repellent, pure emu oil (Zoogen, Inc., Davis, Calif.) was applied to one hand of a volunteer. The other hand was left untreated. Each hand was placed in a nylon mesh cage containing mosquitoes (*Aedes aegypti*) and the number of mosquitoes which landed and/or bit in 30 seconds was recorded. The experiment was performed in duplicate. Results of the experiments were averaged and are summarized in Table 1.

TABLE 1

|  | emu-oil treated hand (lands/bites) | untreated hand (lands/bites) |
| --- | --- | --- |
| Test 1 | 0/0 | 11/11 |
| Test 2 | 1/0 | 26/26 |

These results demonstrate that topically applied emu oil is an effective mosquito repellent. It greatly reduces the number of mosquitoes which land, and completely eliminates biting.

Example 2

The effectiveness of emu oil as a mosquito repellent over time

To determine how long topically applied emu oil maintains efficacy as a mosquito repellent, the treated hand was exposed to a cage of mosquitoes at 15, 30 and 60 minutes after application. The number of lands and bites were compared at each time point with the untreated hand. Results from duplicate experiments were averaged and are presented in Table 2.

TABLE 2

| Time after application | Number of lands on emu-oil treated hand | Number of lands on untreated hand |
| --- | --- | --- |
| 15 | 4 | 18 |
| 30 | 2 | 12 |
| 60 | 10 | 12 |

These results show that emu oil remains an effective mosquito repellent for at least 30 minutes.

Example 3

The effectiveness of diluted emu oil

To determine the effectiveness of diluted emu oil, the emu oil was diluted with ethyl acetate to a fixed percentage, applied to one hand and inserted into a mosquito cage. The number of lands were recorded. The experiments were performed in duplicate at each dilution level. Results are shown in Table 3.

TABLE 3

| Percent emu oil | Number of lands Exp't 1 | Number of lands Exp't 2 | Average Number of lands |
| --- | --- | --- | --- |
| 0 | 10 | 9 | 9.5 |
| 0.50 | 10 | 10 | 10 |
| 1.0 | 5 | 5 | 5 |
| 5.0 | 6 | 4 | 5 |
| 10.0 | 4 | 5 | 4.5 |
| 25.0 | 2 | 1 | 1.5 |
| 50.0 | 1 | 1 | 1 |
| 75.0 | 1 | 1 | 1 |
| 100.0 | 0 | 0 | 0 |

These results demonstrate that dilute amounts of emu oil effectively repel mosquitoes. At a dilution as low as 1%, emu oil reduces by one-half the number of mosquitoes which land. At 25% emu oil, the number of mosquito lands drops to one-tenth of lands on an untreated hand. Thus, emu oil is an effective insect repellent at a concentration of 1% or higher.

Having now fully described this invention, it will be appreciated by those skilled in the art that the same can be performed within a wide range of equivalent parameter, concentrations and conditions without departing from the spirit and scope of the invention and without undue experimentation. While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows the scope of the appended claim.

What is claimed is:

1. A method for repelling biting insects comprising the step of topically applying emu oil to the skin of a subject.

* * * * *